United States Patent [19]
Copelan et al.

[11] Patent Number: 5,133,971
[45] Date of Patent: Jul. 28, 1992

[54] PERSONAL DENTAL HYGIENE ASSEMBLY

[76] Inventors: Phoebe Copelan, 8 Colgate Springs Country Club, Rancho Mirage, Calif. 92270; James B. Copelan, 121 W. Lexington Ave., Glendale, Calif. 91203

[21] Appl. No.: 593,590

[22] Filed: Oct. 2, 1990

Related U.S. Application Data

[63] Continuation of Ser. No. 284,945, Dec. 14, 1988, abandoned.

[51] Int. Cl.⁵ ............................................. A61F 13/02
[52] U.S. Cl. ..................................... 424/448; 424/435; 424/405; 424/443; 549/356; 15/244.1
[58] Field of Search ............. 132/92 R; 424/443, 405, 424/435, 448; 549/356

[56] References Cited

U.S. PATENT DOCUMENTS

| | | | |
|---|---|---|---|
| Re. 33,093 | 10/1989 | Schiraldi | 424/435 |
| 2,700,636 | 1/1955 | Ashton | 424/443 |
| 2,748,774 | 6/1956 | Novak | 424/443 X |
| 2,991,224 | 7/1961 | Bell | 424/435 |
| 3,071,476 | 1/1963 | Werft et al. | 424/435 X |
| 3,203,097 | 8/1965 | Hollander et al. | 424/435 X |
| 3,754,332 | 8/1973 | Warren, Jr. | 424/435 X |
| 3,896,812 | 7/1975 | Kurtz | 424/443 X |
| 4,020,558 | 5/1977 | Cournut et al. | 424/435 X |
| 4,175,326 | 11/1979 | Goodson | 424/435 X |
| 4,235,875 | 11/1980 | Hernestam | 549/356 |
| 4,243,655 | 1/1981 | Gunther | 424/435 |
| 4,554,154 | 11/1985 | White | 424/443 X |

*Primary Examiner*—Thurman K. Page
*Assistant Examiner*—William E. Benston, Jr.
*Attorney, Agent, or Firm*—Wagner & Middlebrook

[57] ABSTRACT

From prior oral hygiene devices, this invention, in its preferred embodiment, is dry and intended for oral use in cleaning and polishing the teeth and for cleaning the gums, tongue, and surrounding mucosa of the mouth and in plaque removal, with the user's own mouth furnishing the only liquid required, which reconstitutes, in situ, the ingredients which are dehydrated and/or impregnated within a membrane.

18 Claims, 2 Drawing Sheets

PERSONAL DENTAL HYGIENE ASSEMBLY

This is continuation of copending application Ser. No. 07/284,945 filed on Dec. 12, 1988 now abandoned.

BACKGROUND OF THE INVENTION

One of the banes of the regular traveler or those working or engaging in sports and away from their residence is the maintenance of regular dental hygiene. This is particularly true for the traveler who may spend many hours without facilities or dental hygiene supplies, such as a toothbrush, dentifrice, mouthwash and dental floss. Most persons note after a few hours, an unpleasant feeling of known bacteria and plaque buildup which is usually accompanied by unpleasant breath, often undetected by the person directly but a condition or risk with which the person is acutely aware. This latter problem has given rise to the increasing popularity of spray type breath deodorizers and "breath mints". The users of such sprays or lozenges fully recognize that the effect is primarily cosmetic or masking and does not attack the real problem of bacteria and plaque removal nor does it provide any cleaning, polishing or improvement in the condition of the surfaces of the teeth, gums, tongue, and surrounding mucosa of the mouth.

There are four primary limitations to good oral hygiene practices away from home. The first is the unavailability of suitable water and disposal facilities for the actual process associated with the cleaning procedures. The second limitation is the lack of privacy for the procedures of brushing, rinsing, expectoration and cleanup. The third limitation is the lack of reasonable cleanliness. The fourth limitation is the lack of convenience of being able to perform the procedures. These principal limitations to good dental hygiene away from home are exemplified by the plight of the business traveler. A 14-hour day of sales calls rarely, if ever, includes a suitable facility with water for brushing, rinsing, expectoration and clean-up. There are few private areas for such procedures. Even if such an area could be found, it is most likely to be in the restroom of a less than frequently cleaned road side filling station, usually inconveniently located, leading to the further frustration of being unable to accomplish any dental hygiene routine or procedure.

PRIOR ART

In the past, many attempts have been made to overcome the difficulties described above, but none have achieved any effective combination for dental hygiene procedures.

Exemplary of the prior art are the following

U.S. Pat. No. 2,527,931 H. Iskoe Oct. 31, 1950

A foldable, disposable toothbrush with a dentifrice in a cup which is dispensable in a coin operated vending machine.

U.S. Pat. No. 4,384,645 J. A. Manfredi May 24, 1983

A portable kit with a toothbrush head which attaches a main hollow body and protected by a cover. The hollow handle encloses a supply of dentifrice.

U.S. Pat. No. 3,646,628 G.C. Hulford Mar. 7, 1972

A foam plastic scrubber for teeth on the end of a plastic round stick. The end of the stick within the foam plastic is pointed and can be used as a tooth pick.

U.S. Pat. 3,699,979 Muhler, et al Oct. 24, 1972

A non-wax dental floss or tape impregnated with a specifically defined dental and polishing agent with a saliva soluble coating for improving the cleaning properties of dental floss.

U.S. Pat. No. 4,554,154 M. White Nov. 19, 1985

A method and product for dental treatment employing a chewable plastic tape carrying an adhesive with remineralizing, immunological and anti-bacterial agents. The adhesive is used to adhere to the teeth and prevent the attachment of plaque.

U.K. Patent 2,048,073 D.W. Kay Dec. 10, 1980

A water absorbing cloth sleeve for the finger impregnated with cleaning agent including a flavoring agent, a bleaching agent and/or a dental abrasive.

Swiss Patent 633,709 C. Beretta Dec. 12, 1982

A sealed foil packet containing a moistened terry cloth like fabric impregnated with a liquid or paste cleaning agent as a substitute for a tooth brush and tooth paste.

Each of these approaches have made progress toward, but have not achieved a truly portable, effective, unobtrusive dental hygiene assembly which may be used comfortably in public, without the need for water as a carrier or for rinsing, with adequate privacy, in an acceptable clean, convenient embodiment to assure its use.

Other patents of ancillary interest include

U.S. Pat. No. 3,057,467 R. R. Williams Oct. 9, 1962

A sealed packet with a paper impregnated with alcohol and water for use in cleansing the hands and face. The patent covering the commercial "Wash'nDri" moist disposable towelette.

U.S. Pat. No. 975,205 C.F. Booth Nov. 8, 1910

A holder for a number of strands of dental floss.

U.S. Pat. No. 1,928,007 P Corsello Sep. 26, 1933

A chewing gum wrapper using dental floss as a tear string.

BRIEF DESCRIPTION OF THE INVENTION

Recognizing the continuing need for an effective and socially acceptable assembly for use in public in performing regular dental hygiene, which was not dependant upon a water supply, secreted privacy, requiring clean individually prepared materials which would be convenient and readily used, in performing regular and periodic dental hygiene procedures, we examined the needs in greater detail. In doing so, we came to the conclusion that a dry, or nearly dry composition fabric of impregnated cleaning agents, dehydrated and/or impregnated upon and into a membrane, was needed to clean and polish the teeth and clean and refresh the gums, tongue and surrounding mucosa of the mouth. A truly useful system needs to rely upon the user's own saliva or the moisture present in the mouth or in unwanted plaque to provide the necessary vehicle to cause reconstitution of the various dehydrated cleaning, polishing, and freshening agents and for the purpose of limited migration throughout the mouth.

We also determined that the dry or near dry composition can be carried in a sealed, but not necessarily vapor tight bag or packet and remain effective for prolonged periods of storage. We further found that the cleaning and polishing ingredients may be effectively carried to the surface of the teeth, gums, tongue and surrounding mucosa of the mouth on a membrane in dry dehydrated or impregnated form with the relative dryness adding to the effectiveness of the polishing agent present.

For a membrane, we found that non-woven cellulose fabric of loose or open porosity is desired so that the membrane may be impregnated with a number of active ingredients in liquid form and subsequently dried for a dry, dehydrated, impregnated membrane of suitable size, e.g. 3 inch by 4 inch, to be partially placed in the mouth.

For a membrane, we likewise found that approximately thirty percent (30%) of the membrane should be saturated, dehydrated and impregnated with the active ingredients. The balance of the membrane should be dry and utilized for clean up of the slight residue if any that may be present upon the lips and finger tips, after use.

A finger, suitable stiff member or the tongue, can be used to massage clean and wipe the teeth, gums, tongue and surrounding mucosa of the mouth with the thirty percent (30%) saturated, dehydrated and impregnated portion of the membrane. There is normally sufficient saliva in the mouth to aid in cleaning and polishing or in accordance with this invention, a humectant may be dehydrated or impregnate within the membrane to aid in saliva generation.

The active ingredients which are dehydrated or impregnated within the membrane may include a flavor and color, however, it is the objective that the residue after cleaning be so slight that upon removal of the membrane, the user feels no need to expectorate or rinse their mouth but rather feels a pleasant fresh taste and feeling of having effectively cleansed their mouth.

In one embodiment, the membrane has secured to it a loop of dental floss which in its pre-formed loop form is ready for flossing, if the user desires. The end of the loop may extend out of the package to form a pull string opener.

In another embodiment, the membrane is in the form of a conical shape secured to a stick for cleaning much like moving a lollipop within the mouth. One surface is designed for polishing the teeth and another surface is particularly designed to massage the gums and deliver as the other embodiments, a dehydrated, impregnated combination of ingredients which are reconstituted by the moisture present in saliva, plaque and the surrounding mucosa of the mouth. The term "dry" within the context of this invention means not only a total absence of liquid, including water, but the presence of such small amounts of liquid that the user need not expectorate or swallow noticeable liquid after use.

BRIEF DESCRIPTION OF THE DRAWING

This invention may be more clearly understood from the following detailed description and by reference to the drawing in which.

DETAILED DESCRIPTION OF THE INVENTION

Figure 1:
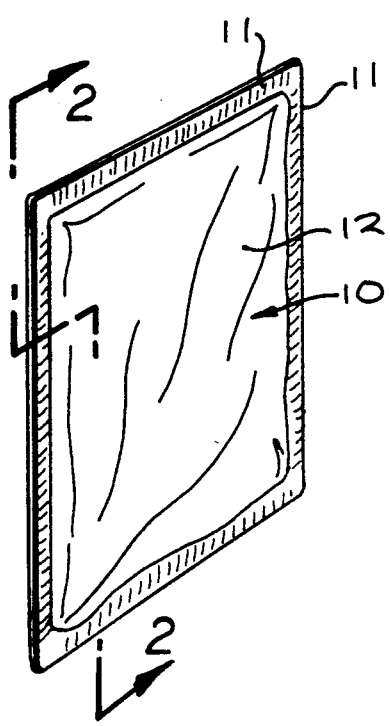
FIG. 1 is a perspective view of a packet of dental hygiene material in accordance with this invention.
Figure 2:
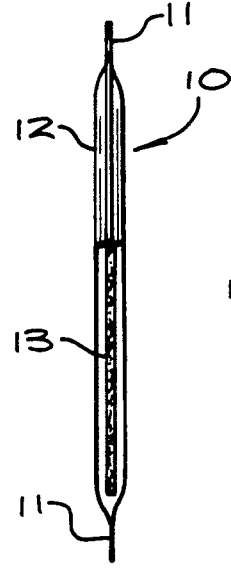
FIG. 2 is a side elevational view of the packet of FIG. 1 with a portion broken away to show the contents.
Figure 3:
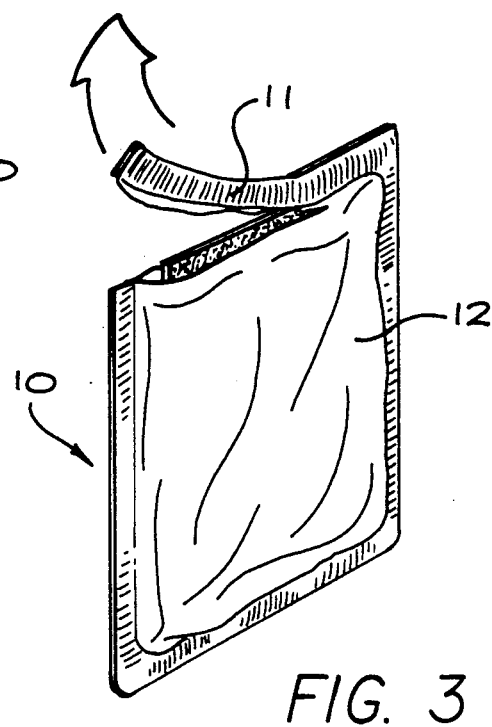
FIG. 3 is a perspective view of the packet of FIG. 1, partially opened by tearing an edge.

Now referring to FIGS. 1-4, the virtual simplicity of this invention becomes apparent in that, as purchased, carried, ready for use, the invention appears as a simple, edge-sealed, packet 10 of protective material such as coated or uncoated paper which is adhesively or mechanically bonded at its edges 11 while forming a generally rectangular pouch 12 for FIGS. 2 and 3. The packet 10 may be of foil or moisture impervious sheet plastic material but need not be so in the basic form of this invention. The packet has dimensions in the order of 1 by 4 inches and may have the general appearance of the hand washing packet of The Kendal Company of Boston, Mass. and sold under the trademark Wash'nDri.

By way of contrast from the Wash'nDri packet, this invention, in its preferred embodiment, is dry and intended for oral use in cleaning and polishing the teeth and for cleaning the gums, tongue, and surrounding mucosa of the mouth and in plaque removal, with the user's own mouth furnishing the only liquid required, which reconstitutes, in situ, the ingredients which are dehydrated and/or impregnated within the membrane.

Figure 4:
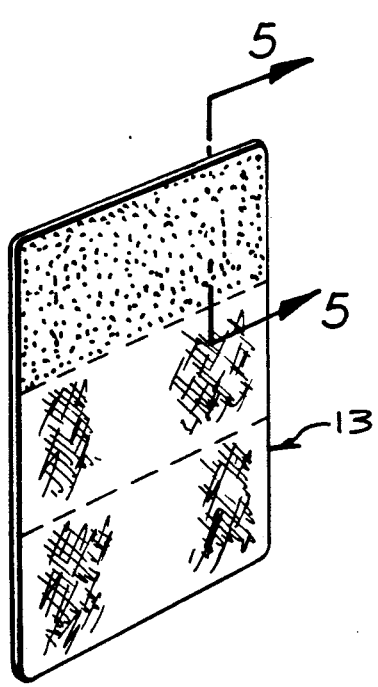
FIG. 4 is a perspective view of the membrane contents of the packet of FIGS. 1-3.
Figure 5:
FIG. 5 is an enlarged fragmentary section of the membrane of FIG. 4 taken along lines 5—5 of FIG. 4; this embodiment of the invention employs a folded, thirty percent (30%) segmented by area, dehydrated impregnated membrane with a loop of dental floss attached. The 30% portion contains the dehydrated, impregnated materials and the remainder of the membrane is for cleaning off the residue, if any, which may be on the lips and/or finger tips area after use.

Contained within the packet 10 is a dentifrice carrier which, in the preferred embodiment of the invention, is in the form of the membrane 13 of FIGS. 2-5 which may be characterized as a slightly abrasive cellulose paper, either non-woven or of a loose weave to present a highly porous structure as is illustrated in FIG. 5. Examples of satisfactory membranes are the following:

1. An unwoven cellulose fiber mat with an embossed striated texture of a weight range of 0.5 to 5 pounds per 100 square feet of surface area, machine cut into individual membranes of 3 inches by 4 inches, folded into thirds, with a packaged shape of approximately 1 inch by 4 inches.

2. A similar sized and weight woven cotton fiber mat with an embossed striated texture.

3. A similar sized and weight woven cotton fiber gauze mat with an embossed striated texture.

4. A similar sized and weight polyester fiber gauze mat with an embossed striated texture.

5. A similar sized and weight cellulose, cotton, woven fiber, polyester blend mat with a striated texture.

6. A polystyrene or similar foam with a porous striated texture in sheet membrane form.

7. A polystyrene foam with a porous striated texture in a chisel/wedge shape with transverse grooves.

THE PREFERRED MEMBRANE BEING

An unwoven cellulose fiber mat with an embossed striated texture of a weight range of 0.5 to 5 pounds per 100 square feet of surface area, machine cut into individual membranes of 3 inches by 4 inches, folded into thirds, with a packaged shape of 1 inch by 4 inches.

Dehydrated, impregnated within the membrane FIG. 4 are a number of compositions which may cooperate in an in situ reconstitution of dehydrated, impregnated compositions, to form a totally effective dental hygiene procedure for:

A) Removing plaque from the surface of the teeth, gums, tongue and surrounding mucosa in the mouth;

B) polishing the exposed surfaces of the teeth;

C) reducing the bacteria count in the mouth;

D) neutralizing the cariogenic bacterial acids present in the mouth;

E) neutralizing the pH levels in the mouth;

F) providing a slight pleasant taste in the mouth;

G) providing a slight pleasant clean sensation in the mouth; and

H) reducing or eliminating breath odors.

Several combinations of the compositions may be impregnated within the membrane to achieve several of the above desirable results. They fall into the following classifications;

I. ANTI CARIES AGENT

Sodium Fluoride (NaF)

Active anti-caries agent: Sodium Fluoride an ionized fluoride ion, when placed on tooth surface (hydroxyapatite crystals or imperfect H.A. Crystals) forms insoluble fluorapatite. Sodium Fluoride is a white, odorless powder, used in fluoridation of water at 2% solution, to reduce the incidence of dental caries.

Stannous Fluoride (SNF2)

Active anti-caries agent: Stannous Fluoride, an ionized fluoride ion, when placed on the tooth surface (hydroxyapatite crystals or imperfect H.A. Crystals) forms insoluble fluorapatite. A compound containing not less than 71.2% stannus tin and between 22.3 and 25.5% fluoride.

II. ETCHING AGENT

Mono and Dibasic Sodium Phosphates (Na2HPO4, 7H20)

The deliberate acid etching of enamel surface prior to or at the same time as the application of ionized fluoride ion will free bonds from the hydroxyapatite, making available for the formation of fluorapatite crystals, thus a greater resistance to cariogenic bacteria.

III. ACID NEUTRALIZING AND pH REGULATING AGENT

Sodium Bicarbonate acts as an acid neutralizing agent. Sodium Bicarbonate aids in the neutralization of plaque acids found on the surface of the teeth, gums, tongue and surrounding mucosa of the oral cavity that produce caries.

IV. CLEANING, POLISHING AND DEODORIZING AGENT

Sodium Bicarbonate also is a preferred agent to act as a cleaning, polishing and deodorizing agent. Sodium Bicarbonate acts as a mild abrasive for cleaning and polishing the teeth.

V. STABILIZING AGENT

POLOXAMER 407 functions as a surfactant, emulsifier or stabilizing agent. Poloxamer 407 is one of a series of non-ionic surfactants of the polyoxypropylene-polyoxyethylene copolymer type sold by the Johnson & Johnson Company of N.J.

VI. SURFACTANT AGENT

POLOXAMER 407 also functions as a surfactant.

VII. EMULSIFIER AGENT

POLOXAMER 407 is effective to function as an emulsifier or stabilizing agent.

VIII. FLAVOR BLENDING AGENT/SWEETENER

SODIUM SACCHARIN (C7H4N Na03A, 2H20) Sodium Saccharin is a calcium salt sweetener which reduces the saltiness of the sodium bicarbonate and other ingredients.

IX. FLAVORING AGENT

Peppermint acts as a flavoring agent for purposes of providing a pleasant mild flavor which aids in favorable and frequent use.

X. COLORING AGENT

FD & C RED COLOR #6 AND #33 act as a coloring agent for purposes of providing a pleasant color without leaving any color trace on the teeth and mouth when used in trace quantities.

XI. ALKALIZING AND EXPECTORANT

SODIUM ACETATE functions as an alkalizing and expectorant agent. Sodium Acetate is a sodium salt which promotes the ejection (loosening) of mucous or exudate and also acts as an alkalizing agent for anti-cariogenic purposes.

XII. ANTI CAKING AGENT

MAGNESIUM OXIDE (MgO) Functions as an anti-caking agent. Magnesium oxide is used as a sorbent (attracts and retains substances by absorption) which aids in the free-flow and anti-caking of other ingredients.

XIII. LUBRICATING AGENTMAGNESIUM

MAGNESIUM SILICATE functions as a lubricating agent and is used as a lubricant in conjunction with Magnesium Oxide and as a suspending agent.

XIV. MEMBRANE

The membrane is of a non-woven cellulose fiber and/or a cotton cloth/gauze, of a size of three (3) inches by four (4) inches which by itself will remove plaque with mechanical manipulation against the teeth, gums, tongue and surrounding mucosa of the oral cavity. The membrane is impregnated by dehydrated or slightly dehydrated materials selected from the group above to increase its effectiveness.

XV. LIQUID CARRYING AGENTS

Water, alcohol, glycerin and/or mineral oil based solutions are suitable carriers for saturation, impregnation and deposition of the above agents upon and into the membrane prior to removal of the liquid carrying agent by evaporation.

PREFERRED COMBINATION OF INGREDIENTS FOR IMPREGNATION OF MEMBRANE

The preferred combination of materials is as follows with an explanation of the functions of each material and why the product increases in effectiveness with the addition of each additional material.

1. MEMBRANE

The membrane is of a non-woven cellulose fiber and/or cotton cloth/gauze, which by itself has slight abrasive qualities to remove plaque with mechanical manipulation against the teeth, gums, tongue and surrounding mucosa of the oral cavity. The membrane is impregnated with the following materials to increase its effectiveness.

2. SODIUM FLUORIDE Acidulated Fluoride

Sodium Fluoride, when added to the membrane, acts as the anti-caries agent. The well known mechanisms of sodium fluoride are 1) the reduction of apatite solubility through conversion of hydroxy-apatite to fluorapatite, 2) remineralization of carious lesions with the deposition of fluoride salts, and 3) antimicrobial activity. The mineral phase of dental enamel is spoken of as hydroxyapatite (Ca10, (PO4)6, (OH02). Hydroxyapatite is however, usually impure to some degree from the acids and bacteria in one's system. The addition of sodium fluoride to the impure hydroxyapatite forms fluorapatite which is relatively insoluble and adds to enamel/tooth strength. Fluoride salts further act on demineralization enamel (carries/decay) by remineralizing that enamel in early carious lesions. Lastly, the fluoride ion in sodium fluoride influences the plaque microbial ecology. The inhibition of sugar metabolism reduces acidogenises with a decrease in enamel demineralization and interference with the plaque polysaccharide formation resulting in a decrease of microbial adhesions to the tooth surface.

3. STANNUS FLUORIDE

With the addition of stannous fluoride, the anti-caries agent and properties are enhanced further. The stannous ion contributes to the formation of the fluorapatite complex and relatively insoluble salts of tin. The stannus ion (salts) make a significant contribution to the arrestment of existing caries lesions.

4. MONO AND DIBASIC PHOSPHATES (Acidulated Phosphate)

When the phosphate ion is added to the membrane, in conjunction with the fluoride ions, it acts as an acid etching agent. The understanding is that the excess phosphate ions would drive the mineral equilibrium of enamel surface toward mineralization with maximum fluorapatite formation. This acid etching of the enamel surface will free some of the weaker bonds of the hydroxyapatite making deficient crystals available to form with the fluoride ions and fluorapatite formation. The increase in fluorapatite crystals on the enamel surface allows a greater resistance of cariogenic attack.

5. SODIUM BICARBONATE

When sodium bioarbonate is added to the membrane, it acts as a cleaning, acid mineralizing, polishing and deodorizing agent. It is true that the membrane itself will function as a polishing vehicle however, with the addition of sodium bicarbonate, there is present a mild abrasive impregnated onto the membrane surface which further enhances the plaque removal. The cleaning and polishing agent of sodium bicarbonate is due to the low abrasive crystals which are very soft and partially soluble in saliva. The solubility of sodium bicarbonate further acts as an acid mineralizing agent by having the ability to neutralize both acid and bases to produce salts and water. The result is a powerful buffer which helps in regulating the pH of the oral cavity and neutralizes plaque acids which are responsible for carious lesions. Studies have shown that a reduced level of bicarbonate ions in the saliva show an increased incidence of dental caries. Finally, the sodium bicarbonate ions acts as a deodorizing agent through the balance of pH.

6. POLOXAMER 407

The function of poloxamer 407 is to act as a surfactant (surface agent) agent. This aids in the loosening of the plaque for easier removal that is on the surface of the teeth, gums, tongue, and surrounding mucosa of the oral cavity.

7. SODIUM SACCHARIN

The addition of sodium saccharin to the membrane provides a sweetener by reducing the saltiness due to the sodium bicarbonate. As previously mentioned, sodium bicarbonate neutralizes acids in the oral cavity to balance pH, which forms salts and water. Sodium saccharin thus aids in reducing the salt flavor when added to the membrane aiding in favorable and frequent use.

8. SORBITOL/MANNITOL

As an alternative to the use of sodium saccharin, the addition of sorbitol/mannitol to the membrane acts similarly as a sweetener by reducing the saltiness of the sodium bicarbonate. Sorbitol/mannitol are sugar alcohols that are generally not absorbed well by the body. These ingredients resist the bacterial action of the oral cavity as well and are non-cariogenic. Additionally, as previously mentioned, sodium bicarbonate neutralizes acids in the oral cavity to balance pH, which forms salts and water. Sorbitol/mannitol thus aids in reducing the salt flavor when added to the membrane, aiding in favorable and frequent use.

9. ASPARTAME

As an alternate, Aspartame may be substituted for sodium saccharin or sorbitol/mannitol. The addition of Aspartame to the membrane acts as a sweetener by reducing the saltiness of the sodium bicarbonate. This ingredient resists the bacterial action of the oral cavity as well and is nocariogenic. Aspartame aids in reducing the salt flavor when added to the membrane, aiding in favorable and frequent use.

10. SORBIC ACID

The addition of sorbic acid to the ingredients functions and acts as a preservative agent for the antimicrobial mechanisms of the sodium fluoride and stannous fluoride. The antimicrobial mechanisms again aid in the inhibition of sugar metabolism thus reducing the amount of acids in the oral cavity and decreases enamel demineralization.

11. SODIUM ACETATE

Sodium acetate may be added to the ingredients to function as an alkalizing and expectorant agent. The sodium acetate is a sodium salt which promotes the ejection (loosening) of mucous or exudate and also acts as an alkalizing agent. The sodium acetate influences the saliva form a sticky, cavity producing state to a thinner state. When the saliva is in a thick consistency there is a greater adherence of bacteria to the surface of the teeth, gums, tongue and surrounding mucosa of the oral cavity, with an increase in tooth demineralization.

12. MAGNESIUM OXIDE

Magnesium oxide may be added to the ingredients to act as an anti-caking and free flowing agent. This allows the other ingredients to work together without being a sticky substance. Since the active ingredients are deposited on the membrane and mobility is the result largely of manual manipulation and dissolving of the ingredients in saliva, an anti-caking agent is usually not required but may be an optional component of the impregnated material.

13. MAGNESIUM SILICATE

Magnesium silicate added to the ingredients functions in conjunction with the magnesium oxide (if present) as a lubricating agent. When the membrane impregnated material is placed on the surface of the teeth, gums, tongue and surrounding mucosa of the oral cavity, and the functions of each ingredient is performed as previously explained, the magnesium oxide and magnesium silicate lubricate the surface of the teeth, gums, tongue and surrounding mucosa of the oral cavity to give them a refreshing feeling.

14. PEPPERMINT FLAVOR (FD & C #6 and #33)

The peppermint or other flavoring and coloring agent may be added to the above ingredients to provide a pleasant flavor and appealing color. When the impregnated membrane is wiped upon the surface of the teeth, gums, tongue and surrounding mucosa of the oral cavity, the peppermint flavor will aid in pleasant and fresh breath thus aiding in favorable and frequent use.

15. WATER/GLYCERIN/OIL VEHICLE

Water, glycerin or mineral oil are added to the ingredients which act as the vehicle for the ingredients to be applied to the membrane. Once applied, the evaporation or partial evaporation of the vehicle will impregnate the membrane with the above listed ingredients and then be allowed to function as mentioned and described.

PREFERRED EMBODIMENT

In the preferred embodiment of this invention, a cellulose paper membrane is used in a 3×4 inch sheet which weighs between 0.5 and 2.0 gms prior to impregnation with the materials. Typically the total weight of the materials added to the membrane ranges from 0.2 to 0.5 gms, made up approximately half and half sodium bicarbonate and flavoring, e.g. peppermint with the remaining agents and compounds present only in trace amounts.

PREFERRED PROCESS

The preferred process for impregnating the membrane is the dip and dry method. In a container holding approximately 250 ml of water, 1 oz. of commercial oil of peppermint, 3 tbs. of sodium bicarbonate plus four drops of food coloring were mixed and a paper membrane partially immersed for a few seconds in the bath. The membrane is withdrawn, dried in a warm commercial household dryer for a minute or two. The dried membrane was removed, folded and ready for packaging. Physically, the membrane shows a pink trace on the portions which were impregnated. The impregnated portion is slightly gritty as compared to the unimpregnated portion.

The other trace ingredients may be added to the water solution.

As an alternate process, the membrane may be passed through a dry bath of the materials and mechanically impregnated as by a pressure roller. The solution including the liquid vehicle plus the materials may be sprayed on the surface of the membrane or transferred by a blotting process.

The dip/dry method is preferred.

ALTERNATE COMBINATIONS OF INGREDIENTS FOR IMPREGNATION OF THE MEMBRANE

Alternate combination #2
Membrane
Sodium Fluoride (0.05%) Active Ingredient
Vehicle
   Glycerin,
   Water or
   Alcohol (6%)
Poloxamer 338
Poloxamer 407
Sodium Benzoate
Sweetener
   Sodium Saccharin,
   Sorbitol/Mannitol or
   Aspertame
Benzoic Acid
Peppermint Flavoring
Coloring (FD & C Red #6 and #33)
Coloring (FD & C Blue #1, FD & C Yellow #5)
Alternate Combination #3
Membrane
Sodium Fluoride (Active ingredient)
Vehicle
   Water,
   Glycerin or
   Hydrated Silica
Alcohol (6%)
Poloxamer 338
Poloxamer 407
Sodium Benzoate
Sweetener
   Sodium Saccharin,
   Sorbitol/Mannitol or
   Aspertame
Benzoic Acid
Flavoring
Coloring All of the solid materials above are water soluble or compatible and, consequently, they may be impregnated within the membrane 13 in an aqueous solution and, upon evaporation of the water, are all deposited in the pores of the membrane 13 as illustrated in FIG. 4. Upon exposure to the moisture, saliva and plaque within the mouth, the ingredients listed above reconstitute in situ, such as the fluoride and flavoring, and due to the enhanced interaction of the expectorating agent, marginally migrate into other areas of the mouth for additional surface and between and around tooth contact, while the polishing agent and lubricants remain largely present in situ at the contact point of the membrane 13, thus allowing a rubbing contact with the surface of the teeth, gums, tongue and surrounding mucosa of the mouth to remove plaque, calcis and food particles from the surface of the teeth, gums, tongue and surrounding mucosa.

Figure 6:
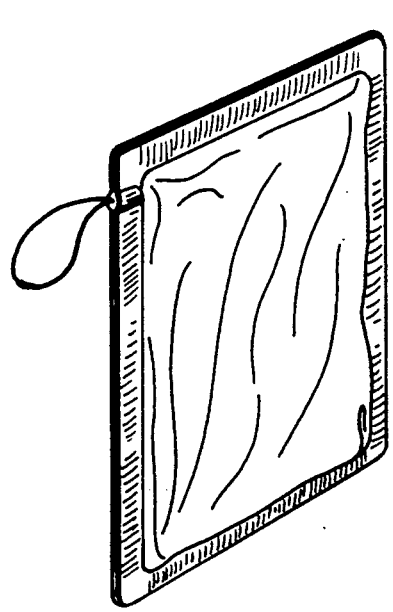
FIG. 6 is a perspective view of an alternate embodiment of this invention using a loop of dental floss as a tear string for the packet of FIG. 1.
Figure 7:
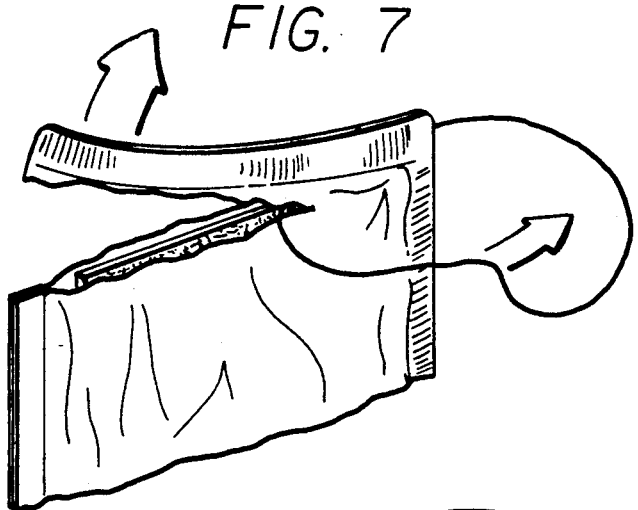
FIG. 7 is a perspective view showing the use of the dental floss tear string to open the packet of FIG. 6.
Figure 8:
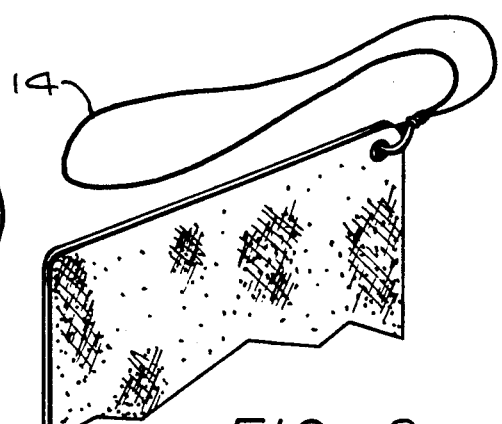
FIG. 8 is a fragmentary perspective view of the membrane of FIGS. 6 and 7 with a dental floss loop attached for use as a holder and for flossing.

Flossing the teeth is possible, employing the embodiment of FIGS. 6-8. In the embodiment of FIG. 6, the packet 10 and internal membrane 13 may be the same as in the embodiment of FIGS. 1-5, but a length or loop of dental floss 14 is secured to the membrane 13. A loop is preferred as shown in FIGS. 7 and 8. In FIG. 6 an end or loop portion 15 extends out of the edge 11 and is usable as a packet opener as shown in FIG. 7 and thereafter used for flossing the teeth. After using the membrane 13 for cleaning and polishing the teeth and flossing the spaces between the teeth with the floss 14, the unimpregnated portion of the membrane 13 may be used to dry the teeth and hands and then the membrane and floss 14 may be discarded in the packet 10.

In the embodiment of FIGS. 6-8, the dental floss is looped through an opening 16 in the membrane 13. The dental floss may likewise be attached by paper embossing without a hole in the membrane 13.

Figure 9:
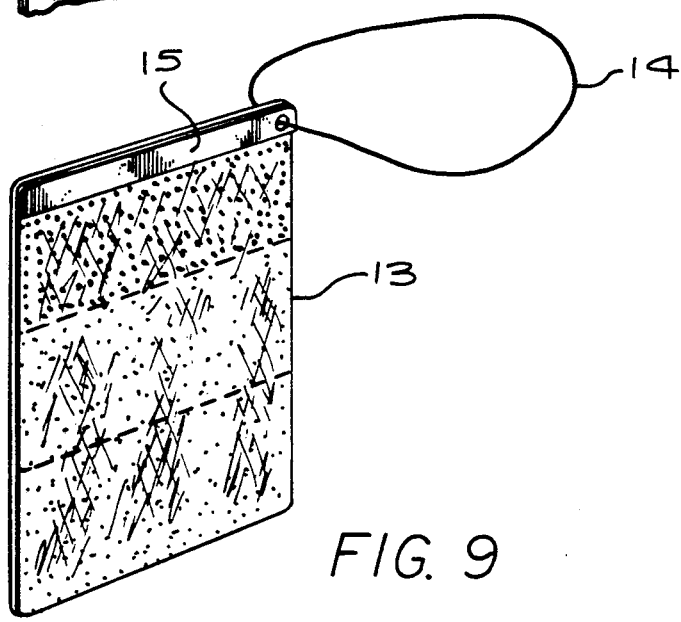
FIG. 9 is a second alternative embodiment of this invention employing a folded, thirty percent (30%) segmented, dehydrated, impregnated membrane with a loop of dental floss attached to a stiffening member. The 30% portion contains the dehydrated, impregnated materials and the remainder of the membrane is for cleaning of the residue, if any, which may be on the lips and/or finger tips after use.

In the embodiment of FIG. 9, a length of dental floss 14 is tied to or through the membrane 13 and further secures a flexible plastic or firm fibrous strip or tab 15 affixed to one edge of the membrane 13 which serves the dual purposes of a handle or firm edge for manipulating the membrane 13 in the mouth or while flossing, using floss length 14, or may be used as a backing for the membrane 13 which may be folded over the length of tab 15, and when placed in the mouth and provides backing for the rubbing action against the teeth, gums, tongue and surrounding mucosa of the mouth.

Figure 10:
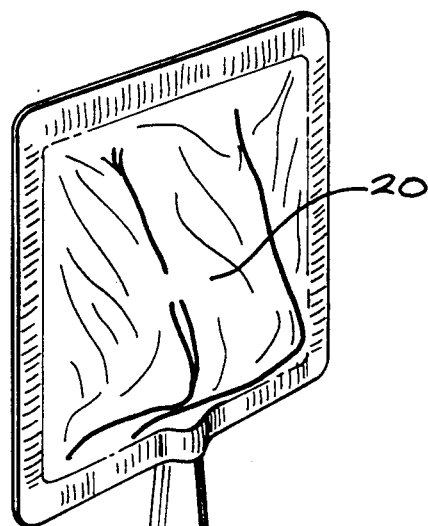
FIG. 10 is a perspective view of a third alternate embodiment of this invention employing a dehydrated, impregnated foam teeth cleaning device with a stick handle.
Figure 11:
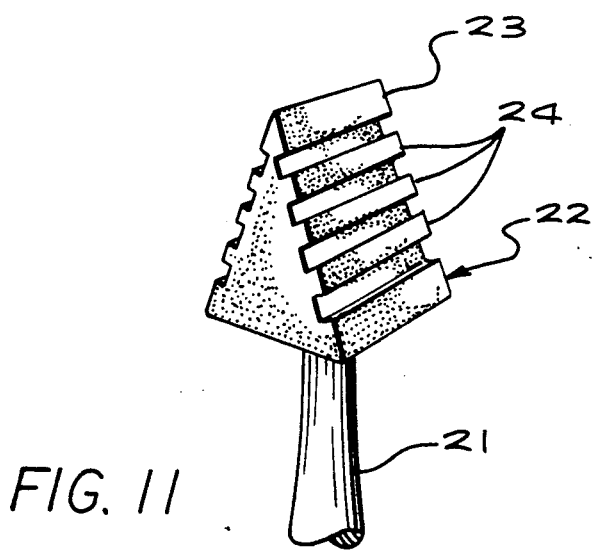
FIG. 11 is a perspective view of the embodiment of FIG. 10 in its protective package.

In each of the embodiments described above the carrier for the hygienic compositions has been a thin paper-like membrane. We have also found that a soft foam plastic carrier of chisel or wedge shaped with transverse grooves can act as an effective dental hygiene device when mounted on a stick handle. Such is shown in FIGS. 10 and 11. In FIG. 10, a packaged device is shown in its sealed pouch 20 the wedged shape head 22 is visible in FIG. 11 with its end point 23 which is ideal for cleaning and massaging the gum line, gums, tongue and surrounding mucosa of the mouth. A plurality of ribs 24 provide discrete polishing surfaces when manipulated with the handle 21. The foam plastic is impregnated with compositions as described above.

Regardless of the form of this invention, the embodiments of FIGS. 1-5, 6-8, 9 or 10-11, an effective portable, disposable, dental hygiene assembly is provided which may be used unobtrusively in public and discarded in its package, after use, with the user assured that he has taken proper steps for reduction of bacteria count, removal of plaque, polishing of the teeth and provision of a fresh taste in the mouth. No external fluid is required and the normal frictional effect of manipulating the membrane within the mouth secures and removes the products of cleaning and the cleaning compositions. Normal ingestion of saliva removes any residual products of cleaning the mouth and cleaning compositions.

The foregoing constitute the best mode known by the applicants for carrying out this invention however, the specific embodiments disclosed are illustrative of the principle of the invention and are not limiting in its scope. To the contrary, it is recognized that one of ordinary skill in the art, given this teaching, may make variations in the structure or compositions without departing from the spirit and scope of this invention. Its scope is defined by the following claims including the protection offered by the doctrine of equivalents.

What is claimed:

1. In a disposable personal dental hygiene assembly, a flexible porous dentifrice carrier of a size adapted to allow a portion thereof to enter the mouth and having surface portions engagable with the distal and proximal tooth surfaces;

said carrier being substantially dry and with at least a portion of its surface being impregnated with a substantially dry mixture of a dentifrice and an expectorant; said impregnating mixture constituting in the order of 40% of the weight of the carrier with the major weight of the impregnating mixture being the dentifrice and the expectorant being in effective trace amount to allow the user's own saliva to moisten the dentifrice sufficiently for tooth cleaning.

2. A disposable personal dental hygiene assembly according to claim 1 in which said carrier is moisture absorbent.

3. A disposable personal dental hygiene assembly according to claim 1 in which said carrier is a substantially flat membrane presenting a porous surface.

4. A disposable personal dental hygiene assembly according to claim 3 in which said carrier is moisture absorbent.

5. A disposable personal dental hygiene assembly according to claim 3 in which said string is dental floss.

6. A disposable personal dental hygiene assembly according to claim 1 in which said carrier is in the form of a soft foam plastic wedge.

7. A disposable personal dental hygiene assembly according to claim 6 in which said wedge is formed with transverse grooves.

8. A disposable personal dental hygiene assembly according to claim 6 including, additionally, a manually engageable handle attached to said wedge at its base.

9. A disposable personal dental hygiene assembly according to claim 6 including, additionally, a rupturable, moisture impervious pouch enclosing said wedge.

10. A disposable personal dental hygiene assembly according to claim 9 including, additionally, means for rupturing said pouch comprising a string embedded in said pouch adjacent an edge thereof and having a manually engageable portion projecting from said pouch.

11. A disposable personal dental hygiene assembly according to claim 10 in which said string is dental floss.

12. In a disposable personal dental hygiene assembly, a flexible porous dentifrice carrier of a size adapted to enter the mouth and having surface portions engageable with the distal and proximal tooth surfaces;

said carrier being substantially dry and with at least a portion of its surface being impregnated with a substantially dry mixture of equal parts of a dentifrice and a flavoring plus an expectorant; the expectorant being in effective trace amount to allow the user's own saliva to moisten the dentifrice sufficiently for tooth cleaning.

13. A disposable personal dental hygiene assembly in accordance with claim 1 or claim 12 wherein in the order of 30% of the surface area of said carrier is impregnated with said substantially dry mixture and the balance of the carrier is available for cleanup of residue.

14. A disposable personal dental hygiene assembly in accordance with claim 12 wherein said impregnating mixture constitutes, by weight, in the order of 40% of the weight of said carrier.

15. A disposable personal dental hygiene assembly in accordance with claim 1 or claim 12 wherein said impregnating mixture includes additionally a trace of an anti caries agent chosen from the group consisting of sodium fluoride and stannous fluoride.

16. A disposable personal dental hygiene assembly in accordance with claim 1 or claim 12 wherein said impregnating mixture includes a trace of an anti caries agent chosen from the group consisting of sodium fluoride and stannous fluoride and includes additionally a trace of an etching agent chosen from the group consisting of mono and dibasic sodium phosphates.

17. A disposable personal dental hygiene assembly in accordance with claim 1 or claim 12 wherein said impregnating mixture includes additionally a trace of a sweetening agent chosen from the group consisting of sodium saccharin, acripitolymahnitol and aspartame sufficient in quantity to overcome the flavor of the tooth cleanser.

18. A disposable personal dental hygiene assembly in accordance with claim 1 wherein said expectorant is sodium acetate.

* * * * *